United States Patent [19]

Davis et al.

[11] Patent Number: 5,241,066

[45] Date of Patent: Aug. 31, 1993

[54] METHOD OF RECOVERING CAPROLACTAM FROM MIXED WASTE

[75] Inventors: Edward A. Davis, Candler; Jack A. Dellinger, Weaverville, both of N.C.

[73] Assignee: BASF Corporation, Parsippany, N.J.

[21] Appl. No.: 904,223

[22] Filed: Jun. 25, 1992

[51] Int. Cl.⁵ .................. C07D 201/12; C07D 201/16
[52] U.S. Cl. ..................................... 540/540; 540/485
[58] Field of Search ............................... 540/540, 485

[56] References Cited

U.S. PATENT DOCUMENTS 3,317,519  5/1967  Lazarus et al. .................. 260/239.3

FOREIGN PATENT DOCUMENTS 143502  11/1971  Czechoslovakia ............... 260/239.3

OTHER PUBLICATIONS

Dmitrieva et al., "Regeneration of ε-Caprolactam From Wastes In the Manufacture of Polycaproamide Fibres and Yarns" *Fibre Chemistry*, Mar. 1986, pp. 229-241.

*Primary Examiner*—Robert T. Bond

[57] ABSTRACT

A process for recovering caprolactam from waste containing both polycaprolactam and materials which are insoluble in acidic solvents for polycaprolactam includes agitating the waste in an acidic solvent capable of dissolving polycaprolactam without degrading the acid insoluble materials, separating the solution containing polycaprolactam from the acid insoluble materials, feeding the solution containing the polycaprolactam to a depolymerization reactor, without substantially precipitating the polycaprolactam and depolymerizing the polycaprolactam solution to obtain substantially pure caprolactam.

12 Claims, No Drawings

METHOD OF RECOVERING CAPROLACTAM FROM MIXED WASTE

FIELD OF THE INVENTION

This invention relates generally to the recovery of monomers from polymeric mixed waste. More particularly, this invention relates to the recovery of caprolactam from mixed wastes containing polycaprolactam.

BACKGROUND OF THE INVENTION

Recovery of useful materials from wastes is a growing goal in modern society. Landfills are becoming filled to capacity and new sites are hard to find. A second motivation for recovering wastes is the global depletion of raw materials needed to make fresh material. Polymer waste, often made from petroleum products, is a fertile area for recovery solutions. Man-made polymers generally do not degrade quickly and petroleum will eventually be depleted.

Mixed wastes present unique problems for recovery. In mixed wastes, it is necessary to recover the desired material without fouling contamination from other components in the waste. One exemplary mixed waste system involves synthetic fiber production.

Compared with single component filaments, fibers made from two components (bicomponent fibers) have improved properties for some applications. One popular bicomponent fiber has a polycaprolactam sheath and a polyethylene terephthalate core. This type of fiber is especially useful in making non-woven webs since nylon 6 melts at a lower temperature than polyethylene terephthalate allowing, on heating to at least the melting point of nylon 6, spot welding where individual filaments cross.

However, in the preparation of these blends, large quantities of material may be produced which are not suitable for commercial use. Also, used materials are targeted for disposal when useful life is over. As discussed, the ever growing presence of manmade waste in landfills affects the disposal of used materials. So, it is an important commercial and environmental consideration to regenerate and recover the constituents of the blend for reuse. The recovery process, however, to be economically acceptable must return the constituents in high yield and purity without excessive loss through decomposition or side reactions. When applied to blends, known processes for separation and recovery of caprolactam do not produce the desired monomers in high yields and adequate purity.

For example, U.S. Pat. No. 3,317,519 to Lazarus et al. describes a recovery process including heating a mixture of polycaprolactam and polyester with an aqueous alkali metal hydroxide at an elevated pressure and precipitating the thus formed homocyclic aromatic dicarboxylic acid by acidification with a strong acid and recovering caprolactam and glycol from the filtrate. This method, because the depolymerization takes place simultaneously (or nearly simultaneously) with the separation of polymers, produces a caprolactam monomer which is tainted with glycols, especially ethylene glycol. The caprolactam monomer is, therefore, unsuitable for reuse in making nylon 6 for fiber applications.

Similarly, Dmitrieva et al. in "Regeneration of $\epsilon$-Caprolactam From Wastes In the Manufacture of Polycaproamide Fibres and Yarns", *Fibre Chemistry*, March 1986, pp. 229-241, describe a method of recovering monomers from a mixture of polycaprolactam and polyester waste wherein the waste mixture is subjected to hydrolysis in the presence of water. This process, simultaneously depolymerizing and recovering, results in caprolactam tainted with ethylene glycol.

Czechoslovakian Paten Application No. 143502 describes a process for recovering polycaprolactam from mixed waste such as is formed when processing old tires containing polycaprolactam cord. The method is based on first dissolving the polyamide in water or a solvent for the polyamide including acid solvents. The non-polyamide portion is separated by filtration. Where acidic solvents are used, the Czechoslovakian application insists that polycaprolactam must be precipitated prior to depolymerization.

Surprisingly and contrary to the above teachings, it has been discovered that substantially pure caprolactam can be recovered from mixed nylon 6 and other waste by dissolution in acidic solvents without the need for precipitation of the dissolved polycaprolactam prior to depolymerization.

SUMMARY OF THE INVENTION

Accordingly, the present invention involves a process for recovering caprolactam from waste containing both polycaprolactam and materials which are insoluble in acidic solvents for polycaprolactam. The process comprises agitating the waste in an acidic solvent capable of dissolving polycaprolactam without degrading the acid insoluble materials and for a time sufficient to dissolve substantially all of the polycaprolactam; separating the solution containing polycaprolactam from the acid insoluble materials; without substantial precipitation, feeding the solution containing the polycaprolactam to a depolymerization reactor; and depolymerizing the polycaprolactam solution to obtain substantially pure caprolactam.

It ia an object of the present invention to recover substantially pure caprolactam from mixtures of polycaprolactam and other wastes.

After reading the following descriptions, related objects and advantages of the present invention will be apparent to those ordinarily skilled in the art to which the invention pertains.

DETAILED DESCRIPTION OF THE PREFERRED EMBODIMENTS

To promote an understanding of the principles of the present invention, descriptions of specific embodiments of the invention follow and specific language describes the same. It will nevertheless be understood that no limitation of the scope of the invention is thereby intended, and that such alterations and further modifications, and such further applications of the principles of the invention as discussed are contemplated as would normally occur to one ordinarily skilled in the art to which the invention pertains.

The present invention involves a process for recovering caprolactam from waste containing both polycaprolactam and non-polyamide materials which are insoluble in acidic solvents for polycaprolactam. The non-polyamide materials present in the mixed waste will depend on the type of waste. Some of the non-polyamide materials which may be present include, for example, natural and synthetic fibers, fillers, pigments, latex rubbers and other materials commonly combined with polycaprolactam when useful articles are manufactured. Especially important are fibrous mixed wastes containing polyethylene terephthalate and, more particularly, bicomponent fibers, such as sheath/core nylon 6/polyester fibers. Sources of such bicomponent fiber waste include scrap from manufacturing the bicomponent. There is no general limitation to the amount of polycaprolactam which must be present to make recovery economical but there should be more than a trace amount of polycaprolactam present in the mixed waste.

The first step of the present invention is agitating the mixed waste in an acidic solvent for a time sufficient to dissolve substantially all of the polycaprolactam. Dissolution is accomplished at either ordinary temperature and pressure (STP) or elevated temperature and pressure, depending on the particular solvent system used. STP is preferable for economic reasons. If the required temperature is above a solvent's boiling pint, the dissolution may be accomplished under elevated pressure.

Acids suitable for use in the process of the present invention may be organic or inorganic and include formic acid, sulfuric acid, hydrochloric acid, acetic acid and phosphoric acid as well as other acids which do not degrade polycaprolactam or the nonpolyamide materials while dissolving polycaprolactam. The acids should be concentrated. For example, phosphoric acid, a preferred solvent, should be concentrated, i.e., at least about 70% by weight of the solvent solution. Also, very weak acids and solvents with acidic potential may be suitable solvents for polycaprolactam when used with certain ionic strength enhancers. For example, ethanol and $CaCl_2$ dissolves polycaprolactam. Other suitable ionic strength enhancers include $LiCl$, $Na_3PO_4$, $Na_2HPO_4$, $NaH_2PO_4$, $Li_3PO_4$, $Li_2HPO_4$, $LiH_2PO_4$, lithium acetate, and lithium formate. Dissolution may be accomplished also using a suitable mixture of solvents. Of course, the amount of acidic solvent used should be sufficient to dissolve the polycaprolactam. This will depend on the amount of waste and the fraction of waste which is polycaprolactam.

The waste is agitated for a time sufficient to dissolve substantially all of the polycaprolactam. For example, in a polycaprolactam/polyethylene terephthalate mixture, dissolution in concentrated phosphoric acid may be accomplished in 5 hours or less at STP.

Following the agitation and dissolution, the acid solution containing polycaprolactam is separated from the insoluble solid waste. The separation may take place according to any known procedure for separating solids from liquids such as filtration, decanting, or cyclone separation. The preferred method of filtration is that which is least costly for the circumstances. Where filtration is used, a filtration device may be located at or near the bottom of the dissolution vessel. The type of filtration device will depend on the size of the undissolved waste particles. It may consist, for example, of a perforated bottom or a wire screen. In any event, it should be sufficient to prevent a significant portion of the solids from passing through. A significant portion is any portion that will interfere with recovering substantially pure caprolactam. After filtration, the solids may be routed for further recovery of the materials contained therein.

After separating, the aqueous acid containing the nylon 6 is fed to a depolymerization reactor where the nylon 6 is depolymerized to obtain substantially pure caprolactam. Known depolymerization procedures may be used and variations thereof will be readily apparent to those ordinarily skilled in the art. One such method is thermal decomposition with superheated steam and a catalyst. A suitable thermal decomposition process is one employing a temperature of 200° C. to 290° C. under autogenous pressure. Usually, depolymerization will be complete in 2-6 hours. Oils and by-products are removed. The caprolactam is concentrated, rectified with lime and distilled. Concentrated ($\geq 75\%$) $H_3PO_4$ is a preferred catalyst.

The depolymerization feedstock may consist of polycaprolactam alone, from the preceding steps. Alternatively, polycaprolactam from other sources may be mixed in.

Coordination of the depolymerization catalyst with the acidic solvent is a preferred aspect of the present invention. Since the depolymerization of polycaprolactam is acid catalyzed, it is extremely convenient and efficient to use an acidic solvent in the dissolution step which is also suitable for a depolymerization catalyst. A preferred acidic solvent for this purpose is concentrated phosphoric acid. Other acids are also suitable.

Following the depolymerization, substantially pure caprolactam is obtained. More specifically, caprolactam recovered by the present invention is generally 99.5% pure. The remaining 0.5% is mostly water. Non-caprolactam and non-water species are present at less than 0.1%. The recovered caprolactam is useful for preparing fiber grade polycaprolactam and other use requiring the use of substantially pure caprolactam.

EXAMPLE

A 250 mL Erlenmeyer flask is charged with 2.788 gms of Colback ® bicomponent fiber (23% polycaprolactam sheath, 77% polyethylene terephthalate ("PET") core) along with 200 mL of 86% phosphoric acid. The mixture is stirred for 5 hours and the solid waste is filtered from the acid solution. The residual waste (PET fibers) is washed with 100 mL of 86% acid, and then rinsed with four 250 mL portions of water. The fiber is dried under high vacuum at 79° C. The dried PET fiber weighs 2.138 gms. The original untreated yarn contains 0.4% finish (0.011 gms). Thus, 2.138 gms of PET remaining out of 2.777 gms of bicomponent fiber is 77% PET. Elemental analysis shows 64.31% carbon, 4.11% hydrogen, 32.23% oxygen and only 0.0097% nitrogen. The treatment removed nearly 100% of the available polycaprolactam.

The polycaprolactam dissolved in phosphoric acid is fed to a depolymerization reactor at a nominal rate equal to 5% (0-25% $H_3PO_4$ based on the amount of nylon present. The polymer is depolymerized and the liberated caprolactam is distilled out by feeding superheated steam with a nominal temperature of 900° F. (350°-500° C.) to the reactor. Oils are separated from the aqueous distillate. The distillate is then concentrated to approximately 80% caprolactam. The concentrated lactam solution is then further concentrated to nominally $\geq 99\%$ caprolactam by distilling the solution through two thin-film evaporators in series. The $\geq 99\%$ lactam is rectified with 5% lime (0-25%) before being distilled a final time in a thin-film evaporator.

The resulting caprolactam is $\geq 99.7\%$ pure, and is suitable for producing fiber-grade nylon 6. The remaining 0.0 to 0.3% of the product is essentially all water, with traces of acceptable contaminants.

What is claimed is:

1. A process for recovering caprolactam from waste containing both polycaprolactam and materials which are insoluble in acidic solvents for polycaprolactam comprising:

(a) agitating the waste in an acidic solvent capable of dissolving polycaprolactam without degrading the acid insoluble materials and for a time sufficient to dissolve substantially all of the polycaprolactam;

(b) separating the solution containing polycaprolactam from the acid insoluble materials;

(c) without substantial precipitation, feeding the solution containing the polycaprolactam to a depolymerization reactor; and (d) depolymerizing the polycaprolactam solution to obtain caprolactam which is substantially free from ethylene glycol.

2. The process of claim 1 wherein the acidic is a concentrated acid selected from:

formic acid;
sulfuric acid;
hydrochloric acid;
acetic acid; and
phosphoric acid.

3. The process of claim 1 wherein said depolymerizing is accomplished with superheated steam and a depolymerization catalyst.

4. The process of claim 3 wherein the acidic solvent is also the catalyst for said depolymerizing.

5. The process of claim 4 wherein the acidic solvent is concentrated phosphoric acid.

6. The process of claim 1 wherein the waste is polycaprolactam/polyethylene terephthalate bicomponent fiber.

7. The process of claim 1 further comprising routing the separated acid materials for recovery of the acid insoluble materials.

8. A process for recovering caprolactam from waste containing both polycaprolactam and polyethylene terephthalate comprising:

(a) agitating the waste in an acidic solvent capable of dissolving polycaprolactam without degrading the polyethylene terephthalate and for a time sufficient to dissolve substantially all of the polycaprolactam;

(b) separating the solution containing polycaprolactam from the acid insoluble materials;

(c) without substantial precipitation, feeding the solution containing the polycaprolactam to a depolymerization reactor; and (d) depolymerizing the polycaprolactam solution to obtain caprolactam which is substantially free from ethylene glycol.

9. The process of claim 8 wherein the acidic solvent is a concentrated acid selected from:

formic acid;
sulfuric acid;
hydrochloric acid;
acetic acid; and
phosphoric acid.

10. The process of claim 8 wherein said depolymerizing is accomplished with superheated steam and a depolymerization catalyst.

11. The process of claim 10 wherein the acidic solvent is also the catalyst for said depolymerizing.

12. The process of claim 11 wherein the acidic solvent is concentrated phosphoric acid.

* * * * *